United States Patent
Hejazi

(10) Patent No.: US 11,707,088 B2
(45) Date of Patent: Jul. 25, 2023

(54) AROMA DELIVERY SYSTEM FOR AEROSOL DELIVERY DEVICE

(71) Applicant: RAI Strategic Holdings, Inc., Winston-Salem, NC (US)

(72) Inventor: Vahid Hejazi, Concord, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 354 days.

(21) Appl. No.: 17/032,522

(22) Filed: Sep. 25, 2020

(65) Prior Publication Data
US 2022/0095677 A1 Mar. 31, 2022

(51) Int. Cl.
*A24F 40/10* (2020.01)
*A24F 40/30* (2020.01)
(Continued)

(52) U.S. Cl.
CPC .............. *A24F 40/30* (2020.01); *A24F 40/10* (2020.01); *A24F 40/42* (2020.01); *A24F 40/50* (2020.01)

(58) Field of Classification Search
CPC .......... A24F 40/10; A24F 40/30; A24F 40/42; A24F 40/50; A61L 9/127; A61M 11/005; A61M 11/042; A61M 11/048; A61M 15/0003; A61M 15/0021; A61M 15/0085; A61M 15/06; A61M 15/08; A61M 2016/0021; A61M 2016/0024; A61M 2016/0027; A61M 2202/0007; A61M 2202/0468; A61M 2205/0211;
(Continued)

(56) References Cited

U.S. PATENT DOCUMENTS

| 2,057,353 A | 10/1936 | Whittemore, Jr. |
| 2,104,266 A | 1/1938 | McCormick |

(Continued)

FOREIGN PATENT DOCUMENTS

| CN | 1541577 A | 11/2004 |
| CN | 2719043 Y | 8/2005 |

(Continued)

OTHER PUBLICATIONS

International Search Report dated Dec. 23, 2021 in the corresponding International Application No. PCT/IB2021/058644, 5 pages.

*Primary Examiner* — Abdullah A Riyami
*Assistant Examiner* — Thang H Nguyen
(74) *Attorney, Agent, or Firm* — Womble Bond Dickinson (US) LLP

(57) ABSTRACT

The present disclosure provides an aerosol precursor consumable, and an aerosol delivery device that comprises a control unit that defines a receiving chamber, and a removable and replaceable aerosol precursor consumable, at least a portion of the consumable configured to be received into the receiving chamber. The aerosol precursor consumable comprises a housing defining an outer wall, an aerosol precursor composition reservoir located in the housing and configured to contain an aerosol precursor composition, an atomizer located in the housing, and at least one aroma diffuser. The atomizer is configured to vaporize the aerosol precursor composition to generate an aerosol for oral delivery to a user, and the at least one aroma diffuser is configured to diffuse an aroma composition for olfactory delivery to the user.

10 Claims, 5 Drawing Sheets

(51) Int. Cl.
*A24F 40/42* (2020.01)
*A24F 40/50* (2020.01)

(58) Field of Classification Search
CPC .. A61M 2205/0238; A61M 2205/0294; A61M 2205/121; A61M 2205/123; A61M 2205/127; A61M 2205/3331; A61M 2205/3584; A61M 2205/3592; A61M 2205/3606; A61M 2205/364; A61M 2205/3653; A61M 2205/368; A61M 2205/505; A61M 2205/581; A61M 2205/582; A61M 2205/583; A61M 2205/584; A61M 2205/587; A61M 2205/588; A61M 2205/6045; A61M 2205/8206; A61M 2209/06; G16H 20/13; G16H 40/63; H05B 2203/014; H05B 2203/021; H05B 3/12
See application file for complete search history.

(56) References Cited

U.S. PATENT DOCUMENTS

| | | | |
|---|---|---|---|
| 3,200,819 A | 8/1965 | Gilbert | |
| 4,922,901 A | 5/1990 | Brooks et al. | |
| 5,060,671 A | 10/1991 | Counts et al. | |
| 5,093,894 A | 3/1992 | Deevi et al. | |
| 5,261,424 A | 11/1993 | Sprinkel, Jr. | |
| 5,388,574 A | 2/1995 | Ingebrethsen et al. | |
| 5,530,225 A | 6/1996 | Hajaligol | |
| 5,687,746 A | 11/1997 | Rose et al. | |
| 5,726,421 A | 3/1998 | Fleischhauer et al. | |
| 5,865,185 A | 2/1999 | Collins et al. | |
| 5,894,841 A | 4/1999 | Voges | |
| 6,125,853 A | 10/2000 | Susa et al. | |
| 6,155,268 A | 12/2000 | Takeuchi | |
| 7,117,867 B2 | 10/2006 | Cox et al. | |
| 7,832,410 B2 | 11/2010 | Hon | |
| 8,314,591 B2 | 11/2012 | Terry et al. | |
| 8,365,742 B2 | 2/2013 | Hon | |
| 8,499,766 B1 | 8/2013 | Newton | |
| 9,554,595 B2* | 1/2017 | Buchberger | A24F 42/20 |
| 10,357,064 B1* | 7/2019 | Kleizo | H05B 3/44 |
| 10,945,462 B2* | 3/2021 | Davis | A24F 40/50 |
| 2005/0016550 A1 | 1/2005 | Katase | |
| 2006/0196518 A1 | 9/2006 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0188490 A1 | 7/2009 | Hon | |
| 2009/0272379 A1 | 11/2009 | Thorens et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0290248 A1 | 12/2011 | Schennum | |
| 2012/0111347 A1* | 5/2012 | Hon | A61M 11/041 131/329 |
| 2012/0260927 A1 | 10/2012 | Liu | |
| 2012/0279512 A1 | 11/2012 | Hon | |
| 2013/0037041 A1 | 2/2013 | Worm et al. | |
| 2013/0056013 A1 | 3/2013 | Terry et al. | |
| 2013/0306084 A1 | 11/2013 | Flick | |
| 2014/0000638 A1 | 1/2014 | Sebastian et al. | |
| 2014/0060554 A1 | 3/2014 | Collett et al. | |
| 2014/0060555 A1 | 3/2014 | Chang et al. | |
| 2014/0096781 A1 | 4/2014 | Sears et al. | |
| 2014/0096782 A1 | 4/2014 | Ampolini et al. | |
| 2014/0166029 A1 | 6/2014 | Weigensberg et al. | |
| 2014/0209105 A1 | 7/2014 | Sears et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2018/0310620 A1* | 11/2018 | Xu | A24F 40/40 |
| 2019/0111171 A1* | 4/2019 | Park | A61B 5/4011 |
| 2019/0183177 A1* | 6/2019 | Hubbard | A61M 15/06 |
| 2020/0222572 A1* | 7/2020 | Bourne | A61L 9/127 |
| 2022/0022537 A1* | 1/2022 | Murray | A24F 40/485 |
| 2022/0125755 A1* | 4/2022 | Hazen | A61K 31/352 |
| 2022/0132933 A1* | 5/2022 | Kiriseko | B05B 1/002 131/329 |

FOREIGN PATENT DOCUMENTS

| | | |
|---|---|---|
| CN | 201379072 Y | 1/2010 |
| DE | 10 2018 100 949 A1 | 7/2019 |
| EP | 0 295 122 A2 | 12/1988 |
| EP | 0 845 220 A1 | 6/1998 |
| EP | 1 618 803 A1 | 1/2006 |
| EP | 2 544 744 B1 | 1/2015 |
| EP | 3 504 988 A1 | 7/2019 |
| GB | 2469850 A | 11/2010 |
| WO | 2003/034847 A1 | 5/2003 |
| WO | 2004/080216 A1 | 9/2004 |
| WO | 2005/099494 A1 | 10/2005 |
| WO | 2007/131449 A1 | 11/2007 |
| WO | WO-2020254671 A1 * | 12/2020 ............. A24F 40/42 |

* cited by examiner

AROMA DELIVERY SYSTEM FOR AEROSOL DELIVERY DEVICE

FIELD OF THE DISCLOSURE

The present disclosure relates to aerosol precursor consumables and aerosol delivery devices such as smoking articles, and more particularly to aerosol delivery devices that utilize electrically generated energy for the production of aerosol (e.g., smoking articles commonly referred to heat-not-burn systems or electronic cigarettes). The smoking articles may be configured to aerosolize an aerosol precursor, which may incorporate materials that may be made or derived from tobacco or otherwise incorporate tobacco, the precursor being capable of forming an inhalable substance for human consumption.

BACKGROUND

Many smoking articles have been proposed through the years as improvements upon, or alternatives to, smoking products based upon combusting tobacco. Example alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Various manners and methods for assembling smoking articles that possess a plurality of sequentially arranged segmented components have been proposed. See, for example, the various types of assembly techniques and methodologies set forth in U.S. Pat. No. 5,469,871 to Barnes et al. and U.S. Pat. No. 7,647,932 to Crooks et al.; and U.S. Pat. App. Pub. Nos. 2010/0186757 to Crooks et al.; 2012/0042885 to Stone et al., and 2012/00673620 to Conner et al.; each of which is incorporated by reference herein in its entirety.

Certain types of cigarettes that employ carbonaceous fuel elements have been commercially marketed under the brand names "Premier," "Eclipse" and "Revo" by R. J. Reynolds Tobacco Company. See, for example, those types of cigarettes described in Chemical and Biological Studies on New Cigarette Prototypes that Heat Instead of Burn Tobacco, R. J. Reynolds Tobacco Company Monograph (1988) and Inhalation Toxicology, 12:5, p. 1-58 (2000). Additionally, a similar type of cigarette has been marketed in Japan by Japan Tobacco Inc. under the brand name "Steam Hot One."

In some instances, some smoking articles, particularly those that employ a traditional paper wrapping material, are also prone to scorching of the paper wrapping material overlying an ignitable fuel source, due to the high temperature attained by the fuel source in proximity to the paper wrapping material. This can reduce enjoyment of the smoking experience for some consumers and can mask or undesirably alter the flavors delivered to the consumer by the aerosol delivery components of the smoking articles. In further instances, traditional types of smoking articles can produce relatively significant levels of gasses, such as carbon monoxide and/or carbon dioxide, during use (e.g., as products of carbon combustion). In still further instances, traditional types of smoking articles may suffer from poor performance with respect to aerosolizing the aerosol forming component(s).

As such, it would be desirable to provide smoking articles that address one or more of the technical problems sometimes associated with traditional types of smoking articles. In addition, it would be desirable to provide a smoking article that is easy to use and that provides reusable and/or replaceable components.

BRIEF SUMMARY

The present disclosure relates to aerosol delivery devices and aerosol precursor consumables for use with aerosol delivery devices. The present disclosure includes, without limitation, the following example implementations:

Example Implementation 1: An aerosol precursor consumable for use with an aerosol delivery device, the aerosol precursor consumable comprising a housing defining an outer wall, an aerosol precursor composition reservoir located in the housing and configured to contain an aerosol precursor composition, an atomizer located in the housing, at least one aroma reservoir located in the housing and configured to contain an aroma composition, and at least one aroma diffuser, wherein the atomizer is configured to vaporize the aerosol precursor composition to generate an aerosol for oral delivery to a user, and wherein the at least one aroma diffuser is configured to diffuse the aroma composition for olfactory delivery to the user.

Example Implementation 2: The aerosol precursor consumable of any preceding example implementation, or any combination of preceding example implementations, wherein the at least one aroma diffuser is located in a recess defined in the outer wall of the housing.

Example Implementation 3: The aerosol precursor consumable of any preceding example implementation, or any combination of preceding example implementations, further comprising a mouthpiece portion, and wherein the aroma diffuser is located upstream from the mouthpiece portion.

Example Implementation 4: The aerosol precursor consumable of any preceding example implementation, or any combination of preceding example implementations, wherein when a user engages the mouthpiece portion of the aerosol precursor consumable, the aroma diffuser is positioned proximate the user's nose.

Example Implementation 5: The aerosol precursor consumable of any preceding example implementation, or any combination of preceding example implementations, wherein the at least one aroma reservoir comprises a plurality of aroma reservoirs, wherein the at least one aroma diffuser comprises a plurality of aroma diffusers, and wherein respective ones of the plurality of aroma diffusers are in liquid communication with respective ones of the plurality of aroma reservoirs.

Example Implementation 6: The aerosol precursor consumable of any preceding example implementation, or any combination of preceding example implementations, wherein the at least one aroma reservoir surrounds at least a portion of the aerosol precursor composition reservoir.

Example Implementation 7: The aerosol precursor consumable of any preceding example implementation, or any combination of preceding example implementations, wherein the aerosol precursor composition comprises an unflavored aerosol precursor composition.

Example Implementation 8: The aerosol precursor consumable of any preceding example implementation, or any combination of preceding example implementations, wherein the at least one aroma diffuser includes at least one temporary protective outer film configured to be removed by a user.

Example Implementation 9: An aerosol delivery device comprising a control unit that defines a housing having a proximal end and a distal end, the proximal end of the housing defining a receiving chamber, at least one aroma aperture extending through the housing into the receiving chamber proximate the proximal end, and a removable and replaceable aerosol precursor consumable, at least a portion of the consumable configured to be received into the receiving chamber, the aerosol precursor consumable comprising a housing defining an outer wall, an aerosol precursor composition reservoir located in the housing and configured to contain an aerosol precursor composition, an atomizer located in the housing, and at least one aroma diffuser, wherein the atomizer is configured to vaporize the aerosol precursor composition to generate an aerosol for oral delivery to a user, wherein the at least one aroma diffuser is configured to diffuse an aroma composition for olfactory delivery to the user, and wherein when the aerosol precursor consumable is engaged with the control unit, the aroma diffuser is positioned proximate the at least one aroma aperture in the control unit housing, such that the aroma composition is delivered to the user through the at least one aroma aperture.

Example Implementation 10: The aerosol delivery device of any preceding example implementation, or any combination of preceding example implementations, wherein the at least one aroma aperture comprises a plurality of aroma apertures.

Example Implementation 11: The aerosol delivery device of any preceding example implementation, or any combination of preceding example implementations, wherein the at least one aroma diffuser is located in a recess defined in the outer wall of the aerosol precursor consumable housing.

Example Implementation 12: The aerosol delivery device of any preceding example implementation, or any combination of preceding example implementations, further comprising a mouthpiece portion, and wherein the aroma diffuser is located upstream from the mouthpiece portion.

Example Implementation 13: The aerosol delivery device of any preceding example implementation, or any combination of preceding example implementations, wherein when a user engages the mouthpiece portion of the aerosol precursor consumable, the aroma diffuser is positioned proximate the user's nose.

Example Implementation 14: The aerosol delivery device of any preceding example implementation, or any combination of preceding example implementations, further comprising at least one aroma reservoir located in the aerosol precursor consumable housing and configured to contain the aroma composition.

Example Implementation 15: The aerosol delivery device of any preceding example implementation, or any combination of preceding example implementations, wherein the at least one aroma reservoir comprises a plurality of aroma reservoirs, wherein the at least one aroma diffuser comprises a plurality of aroma diffusers, and wherein respective ones of the plurality of aroma diffusers are in liquid communication with respective ones of the plurality of aroma reservoirs.

Example Implementation 16: The aerosol delivery device of any preceding example implementation, or any combination of preceding example implementations, wherein the at least one aroma reservoir surrounds at least a portion of the liquid composition reservoir.

Example Implementation 17: The aerosol delivery device of any preceding example implementation, or any combination of preceding example implementations, wherein the aerosol precursor composition comprises an unflavored aerosol precursor composition.

Example Implementation 18: The aerosol delivery device of any preceding example implementation, or any combination of preceding example implementations, wherein the at least one aroma diffuser includes at least one temporary protective outer film configured to be removed by a user.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
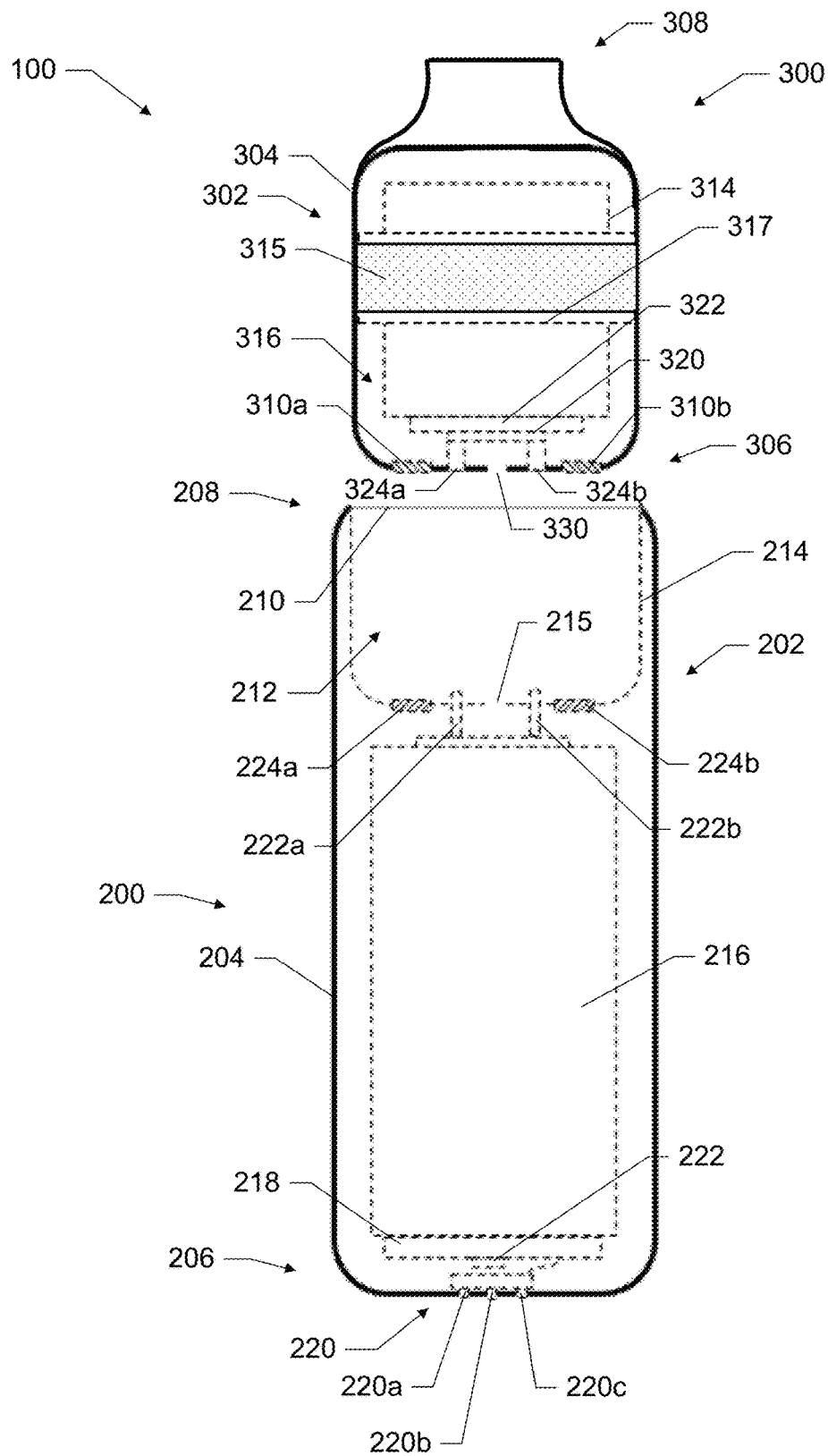
Figure 2:
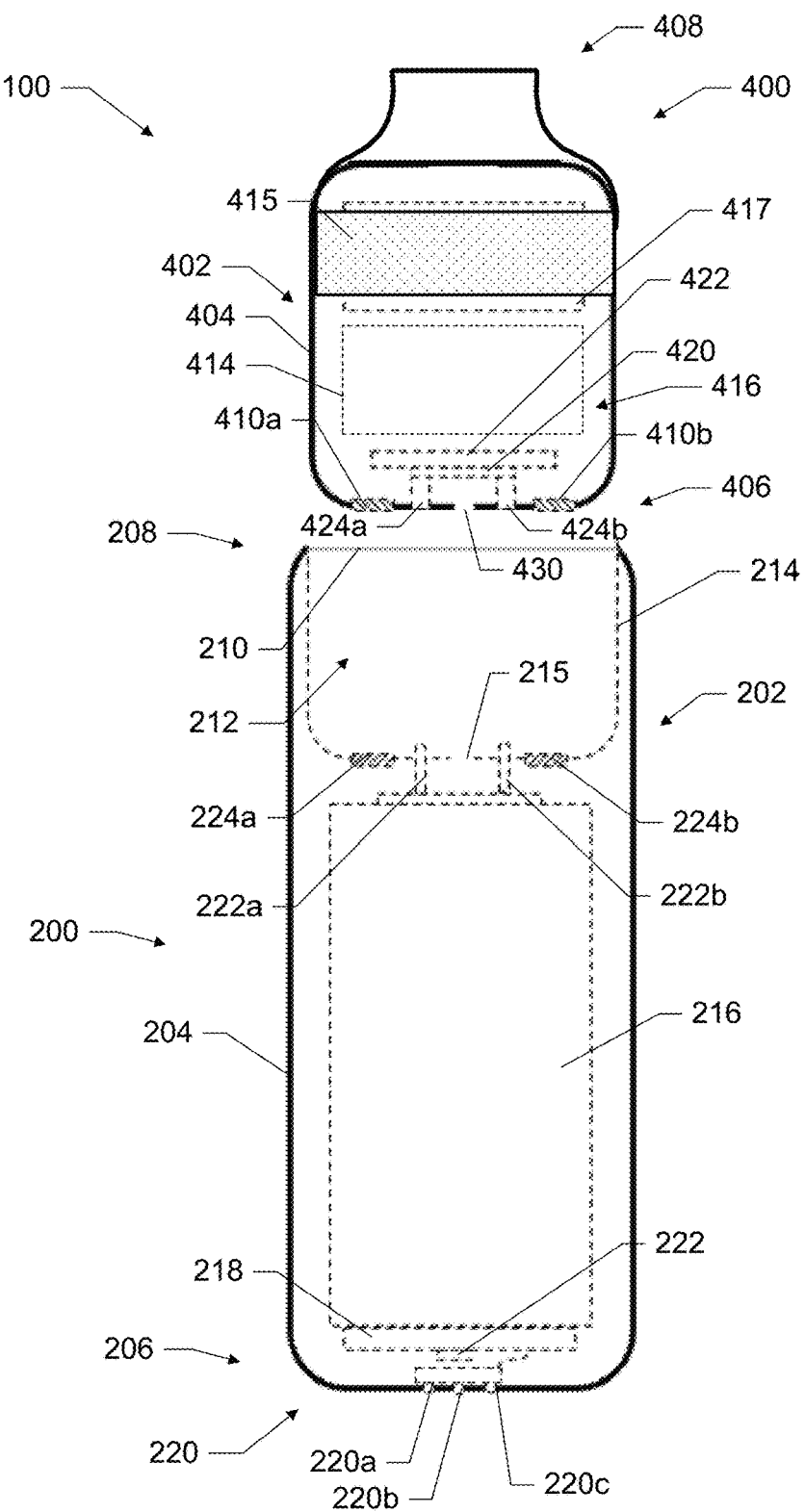
Figure 3:
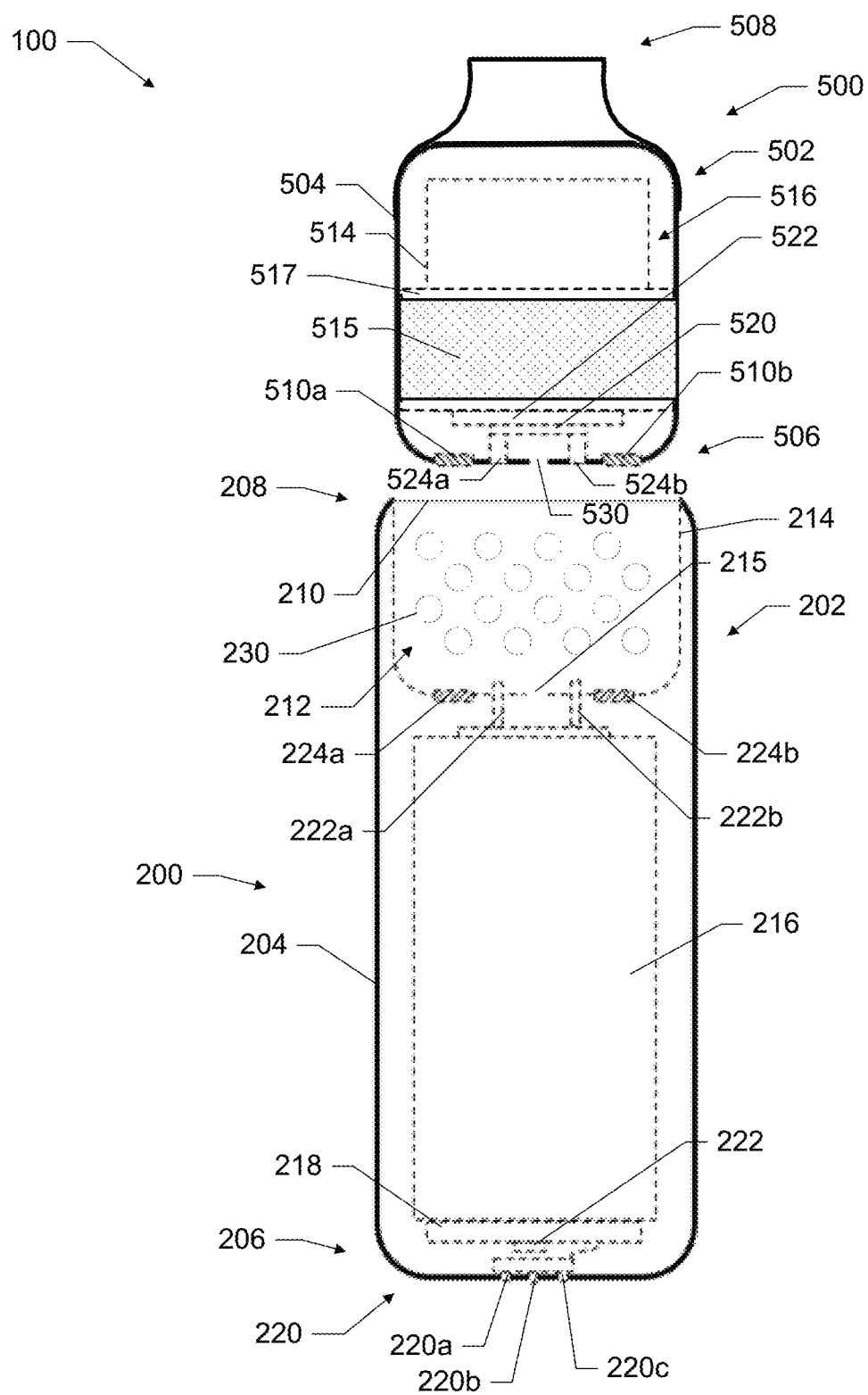
Figure 4:
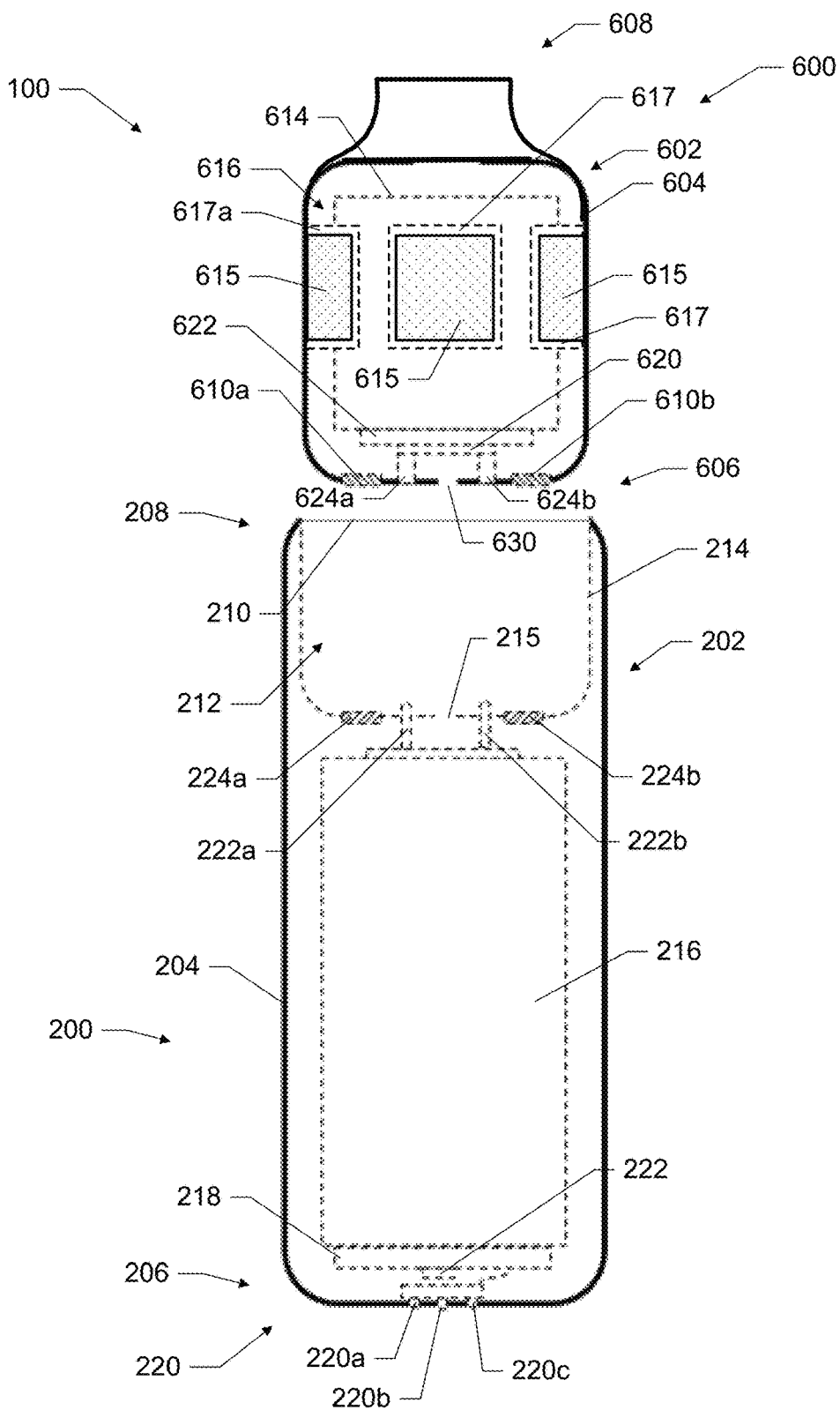
Figure 5:
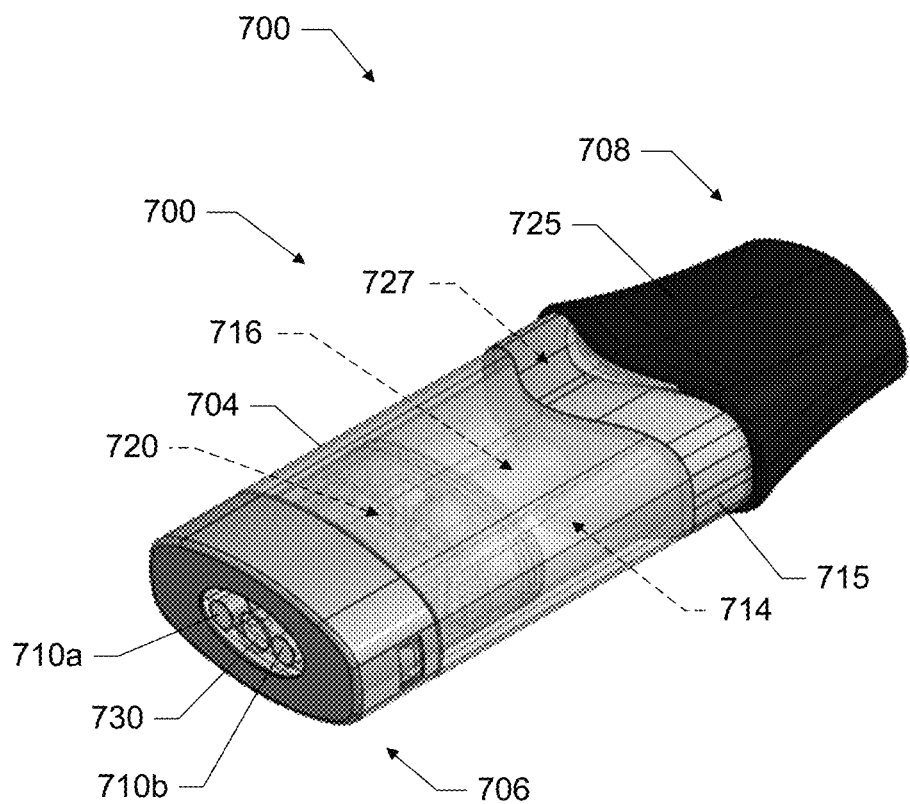

Having thus described the disclosure in the foregoing general terms, reference will now be made to the accompanying drawings, which are not necessarily drawn to scale, and wherein:

FIG. 1 is a front schematic view of an aerosol delivery device, according to an example implementations of the present disclosure;

FIG. 2 is a front schematic view of an aerosol delivery device, according to an example implementation of the present disclosure;

FIG. 3 is a front schematic view of an aerosol delivery device, according to an example implementation of the present disclosure;

FIG. 4 is a front schematic view of an aerosol delivery device, according to an example implementation of the present disclosure; and FIG. 5 is a perspective view of an aerosol precursor consumable, according to an example implementation of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, implementations of the present disclosure relate to aerosol delivery devices or vaporization devices, said terms being used herein interchangeably. Aerosol delivery devices according to the present disclosure use electrical energy and/or an ignitable heat source to vaporize and/or aerosolize a material to form an inhalable substance; and components of such devices have the form of articles that most preferably are sufficiently compact to be considered hand-held devices. In some embodiments, the present aerosol delivery devices may be configured to heat a material (preferably without combusting the material to any significant degree and/or without significant chemical alteration of the material) to form the inhalable substance. Preferably, use of components of preferred aerosol delivery devices does not result in the production of smoke—i.e., from by-products of combustion or pyrolysis of tobacco, but rather, use of those preferred systems results in the production of vapors resulting from volatilization or vaporization of certain components incorporated therein. In some implementations, components of aerosol delivery devices may be characterized as electronic cigarettes, and those electronic cigarettes most preferably incorporate tobacco and/or components derived from tobacco, and hence deliver tobacco derived components in aerosol form.

As noted, some implementations of aerosol delivery devices according to the present disclosure use electrical energy to energize a material to form an inhalable substance. For example, some implementations of aerosol delivery device according to the present disclosure use electrical energy to heat a material to form an inhalable substance (e.g., electrically heated tobacco products), and other implementations of aerosol delivery devices according to the present disclosure use electrical energy to vibrate a material to form an inhalable substance. Still other implementations of aerosol source members according to the present disclosure use an ignitable heat source to heat a material to form an inhalable substance (e.g., carbon heated tobacco products). The material may be heated without combusting the material to any significant degree. As such, the presently disclosed subject matter may be used in relation to a variety of aerosol and/or vapor producing devices, which may include, but is not limited to, devices commonly known as e-cigarettes, heat-not-burn (HNB) devices, carbon tobacco heated products (cTHP), and electric tobacco heated products (eTHP). Non-limiting examples of such devices to which any part or all of the present disclosure may be incorporated are described in U.S. Pat. Nos. 9,839,238, 9,913,493, 10,085,485, and 10,349,674, each of which is incorporated herein in its entirety.

Components of such systems have the form of articles that are sufficiently compact to be considered hand-held devices. That is, use of components of aerosol delivery devices does not result in the production of smoke in the sense that aerosol results principally from by-products of combustion or pyrolysis of tobacco, but rather, use of those systems results in the production of vapors resulting from volatilization or vaporization of certain components incorporated therein. In some example embodiments, components of aerosol delivery devices may be characterized as electronic cigarettes, and those electronic cigarettes may incorporate tobacco and/or components derived from tobacco, and hence deliver tobacco derived components in aerosol form.

Aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure can also be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Some aerosol delivery devices of the present disclosure comprise some combination of a power source (i.e., an electrical power source), at least one control component (e.g., means for actuating, controlling, regulating and ceasing power for heat generation, such as by controlling electrical current flow from the power source to other components of the article—e.g., a microcontroller or microprocessor), an atomizer, a liquid composition (e.g., commonly an aerosol precursor composition liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw). More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of the commercially available electronic aerosol delivery devices, such as those representative products referenced in the background art section of the present disclosure.

One example implementation of an aerosol delivery device 100 of the present disclosure is shown in FIG. 1. In general, the aerosol delivery device 100 of the depicted implementation includes a control unit 200, and a removable aerosol precursor consumable 300. The removable aerosol precursor consumable 300 of the depicted implementation represents one example of an aerosol precursor consumable in the form of a liquid composition cartridge; however, aerosol precursor consumables of other implementations may differ. In the depicted implementation, the aerosol precursor consumable 300 is engageable with the control unit 200 to form an operating aerosol delivery device 100, and the aerosol precursor consumable 300 is removable therefrom.

In the depicted implementation, the control unit 200 includes a body frame 202 that defines a control unit outer wall 204, a control unit distal end 206, and a control unit proximal end 208. The control unit proximal end 208 includes an opening 210 that provides access to a receiving chamber 212 that is defined by a control unit inner frame 214. In the depicted implementation, the receiving chamber is located proximate the proximal end 208 of the control unit 200.

In some implementations, the control unit inner frame 214 may include an aperture 215 that can be configured for transferring pressure differentials therethrough to a pressure sensor positioned within the control unit 200 when air is drawn into the receiving chamber 212. In some implementations, the pressure sensor may be positioned on a printed circuit board (PCB) located in the control unit. In other implementations, however, a pressure sensor may have any location. In addition, some implementations need not include a pressure sensor. Some example configurations of a PCB and a pressure sensor, for example, are described in U.S. Pat. Pub. No. 2015/0245658 to Worm et al., the disclosure of which is incorporated herein by reference in its entirety. In various implementations, a pressure sensor may be positioned anywhere within the control unit so as to subject to airflow and/or a pressure change that can signal a draw on the device and thus cause the atomizer to activate.

The control unit 200 of the depicted implementation also includes a power source, such as a battery 216. Some examples of batteries that can be used according to the disclosure are described in U.S. Pat. Pub. No. 2010/0028766 to Peckerar et al., the disclosure of which is incorporated herein by reference. In the depicted implementation, a draw on the device 100 causes the battery 216 to delivery power to an atomizer located in the aerosol precursor consumable 300. In the absence of a pressure or airflow sensor, the atomizer of some implementations may be activated manually, such as via one or more push buttons. Additional examples of sensing or detection mechanisms, structures, configurations thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; each of which is incorporated herein by reference in its entirety.

The control unit 200 of the depicted implementation also includes at least one control component 218. In the depicted implementation, the control component 218 is located on a printed circuit board (PCB), and the battery 216 is positioned within the control unit body frame 202. In the depicted implementation, the control unit 200 also includes an external connection element 220, which is positioned proximate the distal end 206 of the control unit body frame 202. Although in various implementations an external connection element may have a variety of configurations, in the depicted implementation the external connection element 220 is formed of a plurality of electrical connectors (220a, 220b, 220c). In some implementations, the control unit may include an output element configured to provide visually perceptible output signal. In the depicted implementation, for example, the control unit 200 also includes a light source 222 that may comprise, for example, one or more light emitting diodes (LEDs) capable of emitting one or more colors. In the depicted implementation, the light source 222 is positioned directly on the PCB that contains the control component 218. In various implementations, the PCB may include further control components (e.g., a microcontroller and/or memory components). In the depicted implementation, the LEDs may, for example, be selected of a design to emit light substantially upward from the plane of the PCB. Alternatively, or additionally, suitable LEDs may include reflector elements adapted to or configured to emit light in a substantially different direction, such as parallel to the plane of the PCB, or at a desired angle that provides the desired result. In the depicted implementation, the pressure sensor and the external connection element 220 are likewise directly attached to the PCB or otherwise electrically connected to the PCB.

In the depicted implementation, the control unit 200 further includes electrical pins 222a, 222b that are positioned in the receiving chamber 212 for forming an electrical connection with the aerosol precursor consumable 300 upon insertion of the consumable 300 into the receiving chamber 212. As illustrated, the electrical pins 222a, 222b are positioned proximate a bottom portion of the receiving chamber 212 and extend through a bottom wall of the inner frame 214, which defines the boundaries of the receiving chamber 212. In the depicted implementation, one or more mechanical connectors 224a, 224b are present in the receiving chamber 212, and are positioned in the inner frame 214, and in particular, in the bottom wall thereof. In some implementations, the mechanical connectors may be magnetic elements (e.g., magnets or elements formed of material configured for forming a magnetic connection with a further magnet). Alternatively, or additionally, the mechanical connectors may be positioned in a side wall of the inner frame and thus may be configure for establishing a friction or other mechanical fit with a removable and replaceable aerosol precursor consumable.

In various implementations, the control unit body frame 202 may be formed of any suitable material, such as a metal, plastic, ceramic, glass, or the like. In some implementations, the control unit inner frame is formed of the same material as used to form the control unit body frame; however, in other implementations, different materials may be used. Although the control unit inner frame 214 of the depicted implementation is illustrated as being a separate element from the control unit body frame 202, it is understood that, if desired, the inner frame may be defined by an internal surface of the body frame and may thus form a common part. Some implementations may include an added bottom plate (e.g., such that the bottom plate corresponds to the depicted inner frame bottom wall, and the internal surface of the outer housing corresponds to the illustrated inner frame side wall).

In the depicted implementation, the control unit 200 is configured to receive an aerosol precursor consumable 300 to provide a functioning aerosol delivery device 100. In the depicted implementation, the aerosol precursor consumable 300 defines a body that includes an outer wall 304 and defines a distal end 306 and a proximal end 308. In the depicted implementation, mating connectors 310a, 310b are located proximate the distal end 306 of the aerosol precursor consumable 300 and are configured to form a connection with the mechanical connectors 224a, 224b present in the receiving chamber 212 of the control unit 200. As noted above, mechanical connectors of the control unit of some implementations may comprise magnetic elements. As such, the aerosol precursor consumable of some implementations may include mating magnetic connectors. Alternatively, or additionally, other complementary mechanical connectors may be located on the aerosol precursor consumable (e.g., on one or more sides of the outer wall and thus may be configured for establishing a friction fit or other mechanical fit with the receiving chamber of the control unit).

In the depicted implementation, the aerosol precursor consumable 300 is configured to contain an aerosol precursor composition for vaporization—i.e., an e-liquid, which may be configured as otherwise described herein. The aerosol precursor composition, sometimes referred to as an aerosol precursor liquid composition or a vapor precursor composition or "e-liquid", may comprise a variety of components, which may include, by way of example, a polyhydric alcohol (e.g., glycerin, propylene glycol, or a mixture thereof), nicotine, tobacco, tobacco extract, and/or flavorants. Representative types of aerosol precursor components and formulations are also set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor composition incorporated within the aerosol delivery system is such that the aerosol generating device provides acceptable sensory and desirable performance characteristics. For example, sufficient amounts of aerosol forming material (e.g., glycerin and/or propylene glycol) may be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating device. In one or more embodiments, about 1 ml or more, about 2 ml or more, about 5 ml or more, or about 10 ml or more of the aerosol precursor composition may be included.

In the some of the examples described above, the aerosol precursor composition comprises a glycerol-based liquid. In other implementations, however, the aerosol precursor composition may be a water-based liquid. In some implementations, the water-based liquid may be comprised of more than approximately 80% water. For example, in some implementations the percentage of water in the water-based liquid may be in the inclusive range of approximately 90% to approximately 93%. In some implementations, the water-based liquid may include up to approximately 10% propylene glycol. For example, in some implementations the percentage of propylene glycol in the water-based liquid may be in the inclusive range of approximately 4% to approximately 5%. In some implementations, the water-based liquid may include up to approximately 10% flavorant. For example, in some implementations the percentage of flavorant(s) of the water-based liquid may be in the inclusive range of approximately 3% to approximately 7%. In some implementations, the water-based liquid may include up to approximately 1% nicotine. For example, in some implementations the percentage nicotine in the water-based liquid may be in the inclusive range of approximately 0.1% to approximately 1%. In some implementations, the water-based liquid may include up to approximately 10% cyclodextrin. For example, in some implementations the percentage cyclodextrin in the water-based liquid may be in the inclusive range of approximately 3% to 5%. In still other implementations, the aerosol precursor composition may be a combination of a glycerol-based liquid and a water-based liquid. For example, some implementations may include up to approximately 50% water and less than approximately 20% glycerol. The remaining components may include one or more of propylene glycol, flavorants, nicotine, cyclodextrin, etc. Some examples of water-based liquid compositions that may be suitable are disclosed in GB 1817863.2, filed Nov. 1, 2018, titled Aerosolisable Formulation; GB 1817864.0, filed Nov. 1, 2018, titled Aerosolisable Formulation; GB 1817867.3, filed Nov. 1, 2018, titled Aerosolisable Formulation; GB 1817865.7, filed Nov. 1, 2018, titled Aerosolisable Formulation; GB 1817859.0, filed Nov. 1, 2018, titled Aerosolisable Formulation; GB 1817866.5, filed Nov. 1, 2018, titled Aerosolisable Formulation; GB 1817861.6, filed Nov. 1, 2018, titled Gel and Crystalline Powder; GB 1817862.4, filed Nov. 1, 2018, titled Aerosolisable Formulation; GB 1817868.1, filed Nov. 1, 2018, titled Aerosolised Formulation; and GB 1817860.8, filed Nov. 1, 2018, titled Aerosolised Formulation, each of which is incorporated by reference herein in its entirety.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), melatonin, stimulants (e.g., caffeine, theine, and guarana), amino acids (e.g., taurine, theanine, phenylalanine, tyrosine, and tryptophan) and/or pharmaceutical, nutraceutical, nootropic, psychoactive, and medicinal ingredients (e.g., vitamins, such as B6, B12, and C and cannabinoids, such as tetrahydrocannabinol (THC) and cannabidiol (CBD)). It should be noted that the aerosol precursor composition may comprise any constituents, derivatives, or combinations of any of the above.

As noted herein, the aerosol precursor composition may comprise or be derived from one or more botanicals or constituents, derivatives, or extracts thereof. As used herein, the term "botanical" includes any material derived from plants including, but not limited to, extracts, leaves, bark, fibres, stems, roots, seeds, flowers, fruits, pollen, husk, shells or the like. Alternatively, the material may comprise an active compound naturally existing in a botanical, obtained synthetically. The material may be in the form of liquid, gas, solid, powder, dust, crushed particles, granules, pellets, shreds, strips, sheets, or the like. Example botanicals are tobacco, eucalyptus, star anise, hemp, cocoa, cannabis, fennel, lemongrass, peppermint, spearmint, rooibos, chamomile, flax, ginger, *Ginkgo biloba*, hazel, hibiscus, laurel, licorice (liquorice), matcha, mate, orange skin, papaya, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, curcuma, turmeric, sandalwood, cilantro, bergamot, orange blossom, myrtle, cassis, valerian, pimento, mace, damien, marjoram, olive, lemon balm, lemon basil, chive, carvi, verbena, tarragon, geranium, mulberry, ginseng, theanine, theacrine, maca, ashwagandha, damiana, guarana, chlorophyll, baobab or any combination thereof. The mint may be chosen from the following mint varieties: *Mentha arvensis, Mentha* c.v., *Mentha niliaca, Mentha piperita, Mentha piperita citrata* c.v., *Mentha piperita* c.v, *Mentha spicata crispa, Mentha cardifolia, Mentha longifolia, Mentha suaveolens variegata, Mentha pulegium, Mentha spicata* c.v. and *Mentha suaveolens.*

As noted above, in various implementations, the aerosol precursor composition may include a flavorant or materials that alter the sensory or organoleptic character or nature of the aerosol of the smoking article. In some implementations, the flavorant may be pre-mixed with the liquid. In other implementations, the flavorant may be delivered separately downstream from the atomizer as a main or secondary flavor. Still other implementations may combine a pre-mixed flavorant with a downstream flavorant. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime, lemon, mango, and other citrus flavors), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, ginseng, chamomile, turmeric, *Bacopa monniera, Ginkgo biloba, Withania somnifera*, cinnamon, sandalwood, jasmine, cascarilla, cocoa, licorice, and flavorings and flavor packages of the type and character traditionally used for the flavoring of cigarette, cigar, and pipe tobaccos. Other examples include flavorants derived from, or simulating, burley, oriental tobacco, flue cured tobacco, etc. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

As used herein, the terms "flavor," "flavorant," "flavoring agents," etc. refer to materials which, where local regulations permit, may be used to create a desired taste, aroma, or other somatosensorial sensation in a product for adult consumers. They may include naturally occurring flavor materials, botanicals, extracts of botanicals, synthetically obtained materials, or combinations thereof (e.g., tobacco, cannabis, licorice (liquorice), hydrangea, eugenol, Japanese white bark magnolia leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, papaya, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, betel, shisha, pine, honey essence, rose oil, vanilla, lemon oil, orange oil, orange blossom, cherry blossom, cassia, caraway, cognac, jasmine, ylang-ylang, sage, fennel, wasabi, piment, ginger, coriander, coffee, hemp, a mint oil from any species of the genus *Mentha*, eucalyptus, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, curcuma, cilantro, myrtle, cassis, valerian, pimento, mace, damien, marjoram, olive, lemon balm, lemon basil, chive, carvi, verbena, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, liquid such as an oil, solid such as a powder, or gas.

In some implementations, the flavor comprises menthol, spearmint and/or peppermint. In some embodiments, the flavor comprises flavor components of cucumber, blueberry, citrus fruits and/or redberry. In some embodiments, the flavor comprises eugenol. In some embodiments, the flavor comprises flavor components extracted from tobacco. In some embodiments, the flavor comprises flavor components extracted from cannabis.

In some implementations, the flavor may comprise a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to, eucolyptol or WS-3.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In the depicted implementation, the aerosol precursor consumable 300 includes an aerosol precursor composition reservoir 314 wherein the aerosol precursor composition may be retained. In the depicted implementation, an aerosol passage 316 at least partially surrounds the reservoir 314 in a longitudinal direction from the distal end 306 to the proximal end 308 of the consumable 300. In other implementations, however, it is understood that the aerosol passage may extend through at least a portion of the reservoir such that the reservoir is configured in an annular space between the aerosol passage and the consumable outer wall.

The aerosol precursor consumable 300 of the depicted implementation further includes an aroma diffuser 315 configured to diffuse an aroma composition for olfactory delivery to a user. In such a manner, the location of the aroma diffuser of some implementations may be positioned upstream from an aerosol outlet of the consumable. For example, in some implementations the aroma diffuser may be located proximate a user's nose when a user engages the consumable for delivery of the aerosol. In various implementations, the aroma diffuser may have any size or shape. In the depicted implementation, the aroma diffuser 315 has a substantially rectangular shape and cross-section shape and is located proximate the proximal end 308 of the aerosol precursor consumable 300, extending around the periphery of the consumable outer wall 304 (e.g., a strip that extends around the periphery of the consumable). In some implementations, the aroma composition may be impregnated into the aroma diffuser. For example, in some implementations the aroma diffuser may comprise a porous material with high aroma composition absorption/uptake characteristics. In the depicted implementation, the aroma diffuser 315 is configured to transport (e.g., wick) the aroma composition from an aroma reservoir 317 for olfactory delivery to a user. In various implementations, the aroma diffuser may have a high porosity or a low porosity and may be made of a variety of materials or combinations of materials, including, but not limited to, polyethylene, polyethylene terephthalate, polypropylene, poly ether sulfone, cellulose, cotton, ceramics, silica, etc. For example, in some implementations, the aroma diffuser may be made of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. In various implementations, the aroma diffuser may be any material that contains an open pore network (i.e., a plurality of pores that are interconnected so that fluid may flow from one pore to another in a plurality of direction through the element). In some implementations, the aroma diffuser may be made of fibers of these materials or fibers of combinations of these materials. As noted, the aroma reservoir 317 of the depicted implementation is configured to store the aroma composition. In the depicted implementation, the aroma reservoir 317 is separate from the aerosol precursor composition reservoir 314, and surrounds at least a portion of the aerosol precursor composition reservoir 314 to form an annular storage area. In other implementations, however, other configurations are possible. For example, in some implementations, the aroma reservoir may comprise a storage area located on one side of the cartridge, such as, for example, a storage area having a semi-circular cross-section shape. In some implementations, the aroma diffuser may further include at least one temporary protective outer film configured to cover the aroma diffuser (such as, for example, during shipping and/or storage) and that is configured to be removed by a user.

In some implementations, the aerosol precursor composition may be scentless and/or flavorless, or the aerosol precursor composition may have a diminished flavor and/or scent. In such a manner, the aroma composition may comprise the primary olfactory sensation delivered to the user. In other implementations, the aerosol precursor composition may include a primary flavor and/or a scent, and the aroma composition may comprise a secondary or supplementary olfactory sensation delivered to the user. In various implementations, the aroma composition may include any aroma or combinations of aromas configured for delivery to a user via the aroma diffuser. Some examples include aroma compositions that comprise, simulate, and/or are derived from botanical ingredients. Alternatively, some aroma compositions may comprise an active compound naturally existing in a botanical, obtained synthetically. In various implementations, the aroma composition may be in the form of liquid, gas, solid, powder, dust, crushed particles, granules, pellets, shreds, strips, sheets, or the like. Example botanicals are tobacco, eucalyptus, star anise, hemp, cocoa, cannabis, fennel, lemongrass, peppermint, spearmint, rooibos, chamomile, flax, ginger, *Ginkgo biloba*, hazel, hibiscus, laurel, licorice (liquorice), matcha, mate, orange skin, papaya, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, curcuma, turmeric, sandalwood, cilantro, bergamot, orange blossom, myrtle, cassis, valerian, pimento, mace, damien, marjoram, olive, lemon balm, lemon basil, chive, carvi, verbena, tarragon, geranium, mulberry, ginseng, theanine, theacrine, maca, ashwagandha, damiana, guarana, chlorophyll, baobab or any combination thereof. The mint may be chosen from the following mint varieties: *Mentha arvensis, Mentha* c.v., *Mentha niliaca, Mentha piperita, Mentha piperita citrata* c.v., *Mentha piperita* c.v., *Mentha spicata crispa, Mentha cardifolia, Mentha longifolia, Mentha suaveolens variegata, Mentha pulegium, Mentha spicata* c.v., and *Mentha suaveolens.*

Other examples of possible aroma compositions include, but are not limited to, vanillin, ethyl vanillin, cream, tea, coffee, fruit (e.g., apple, cherry, strawberry, peach and citrus aromas, including lime, lemon, mango, and other citrus aromas), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, ginseng, chamomile, turmeric, *Bacopa monniera, Ginkgo biloba, Withania somnifera*, cinnamon, sandalwood, jasmine, cascarilla, cocoa, licorice, and aromas of the type and character traditionally experienced with cigarette, cigar, and pipe tobaccos. Further examples include aroma compositions that include naturally occurring materials, botanicals, extracts of botanicals, synthetically obtained materials, or combinations thereof (e.g., tobacco, cannabis, licorice (liquorice), hydrangea, eugenol, Japanese white bark magnolia leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, papaya, rhubarb, grape, durian, dragon fruit, cucumber, blueberry, redberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, betel, shisha, pine, honey essence, rose oil, vanilla, lemon oil, orange oil, orange blossom, cherry blossom, cassia, caraway, cognac, jasmine, ylang-ylang, sage, fennel, wasabi, piment, ginger, coriander, coffee, hemp, a mint oil from any species of the genus *Mentha*, eucalyptus, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, curcuma, cilantro, myrtle, cassis, valerian, pimento, mace, damien, marjoram, olive, lemon balm, lemon basil, chive, carvi, verbena, tarragon, limonene, thymol, camphene). They may be imitation, synthetic or natural ingredients or blends thereof. They may be in any suitable form, for example, liquid such as an oil, solid such as a powder, or gas.

In the depicted implementation, the consumable 300 further includes a mouthpiece portion that is defined as a portion of the proximal end 308 of the consumable 300 that a user engages in order to draw on the device 100. Although in the depicted implementation the mouthpiece portion is integral with the consumable body 302, in other implementations the mouthpiece portion may be a separate element from the consumable body. In such implementations, the mouthpiece portion may be attachable to the consumable body. In the depicted implementation, the aerosol precursor consumable 300 further includes an atomizer 320 configured to aerosolize the aerosol precursor composition and that includes a liquid transport element 322. In the depicted implementation, the atomizer 320 comprises a heater and the liquid transport element 322 defines a fluid connection between the heater and liquid in the reservoir 314. In other implementations, the atomizer may comprise a vibrating assembly (with or without a perforated mesh) and the liquid transport element may define a fluid connection between the vibrating assembly and liquid in the reservoir.

In the depicted implementation, the atomizer 320 and liquid transport element 322 are configured as separate elements that are fluidly connected. In other implementations, these components may be combined. Still other implementations need not include a liquid transport element. In the depicted implementation, the aerosol precursor consumable 300 includes one or more electrical contacts 324*a*, 324*b* that are configured to electrically connect the atomizer 320 with the battery 216 in the control unit 200 through contact with the electrical pins 222*a*, 222*b* when the aerosol precursor consumable 300 is received in the receiving chamber 212 of the control unit 200.

In various implementations, a liquid transport element may be formed of one or more materials configured for transport of a liquid, such as by capillary action. In some implementations, for example, a liquid transport element may be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element thus may be any material that contains an open pore network (i.e., a plurality of pores that are interconnected so that fluid may flow from one pore to another in a plurality of direction through the element). Some implementations of the present disclosure may particularly relate to the use of non-fibrous transport elements. As such, fibrous transport elements can be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. Pub. Nos. 2014/0261487 to Chapman et al.; 2014/0059780 to Davis et al.; and 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference. In some implementations, a liquid transport element can be formed partially or completely from a porous monolith, such as a porous ceramic, a porous glass, or the like. Example monolithic materials suitable for use according to embodiments of the present disclosure are described, for example, in U.S. Pat. Pub. Nos. 2014/0123989 to LaMothe and 2017/0188626 to Davis et al., the disclosures of which are incorporated herein by reference. The porous monolith can form a substantially solid wick.

As noted, in the depicted implementation the atomizer 320 comprises a heater. Various implementations of materials configured to produce heat when electrical current is applied therethrough may be employed to form the heater of the depicted implementation. In some implementations, for example, the heater may comprise a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further implementations, the heater may be formed from conductive inks, boron doped silica, and/or ceramics (e.g., positive or negative temperature coefficient ceramics). Other types of heaters may also be utilized, such as, for example, laser diodes and/or microheaters. A laser diode may be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode may particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The heater in particular may be configured to be substantially flat. Such heaters are described in U.S. Pat. Pub. No. 2016/0345633 to DePiano et al., which is incorporated herein by reference.

As noted, further types of atomizers are also encompassed by the present disclosure. For example, in some implementations, an atomizer may comprise one or more elements adapted to or configured vaporize or aerosolize (or otherwise form a fine, particulate form of) an aerosol precursor liquid without necessarily heating the liquid. For example, a piezo element may be used as a vaporizer in certain embodiments of the present disclosure, and suitable piezo elements are described, for example, in U.S. Pat. Pub. No. 2013/0319404 to Feriani et al. and U.S. Pat. Pub. No. 2019/0014819 to Sur, the disclosure of each of which is incorporate herein by reference in its entirety.

In the depicted implementation, the outer wall 304 of the aerosol precursor consumable 300 is configured to be at least partially transparent or translucent so that the liquid composition contained therein is visible externally. As such, in the depicted implementation the entire outer tank wall 304 is transparent or translucent. Alternatively, only a single side of the outer tank wall may be transparent, translucent, or tinted while the remaining portions of the outer tank wall may be substantially opaque.

In some implementations, the body frame may include an aperture (e.g., a cut-out, opening, or notch) to allow for viewing of the consumable when inserted into the control unit; however, in other implementations, the aperture may be expressly excluded. In some implementations, the aperture may comprise a cut-out. Some implementations of the cut-out may be substantially oval-shaped; however, it is understood that any shape is encompassed herein. In some implementations, the aperture may be configured as a notch extending from the proximal end of the outer wall of the control unit some distance toward the distal end of the control unit. In other implementations, the aperture may be configured so as not to have any open borders and thus may expressly exclude a notch configuration as noted above. In some implementations, the aperture may be completely open or the aperture may have a transparent member (e.g., glass or plastic) positioned in the opening defined by the window or covering the window on one or both of the inner surface and outer surface of the outer wall of the device. In some implementations, the housing panel may include an output feature configured to allow an output signal of the control unit to pass therethrough.

In some implementations, the control unit may include a light window configured to substantially align with the light source of the control unit. Although some implementations need not include a light window and other implementations need not include additional components, the control unit may further include a light tube configured to transmit light emitting from the light source through the body frame. Other implementations may include other features configured to allow light from a light source to pass therethrough.

As noted, the aerosol delivery device 100 of the depicted implementation includes a control component 218 for controlling the amount of electric power to the heater during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

In use, when an aerosol precursor consumable 300 is inserted into the receiving chamber 212 of the control unit 200, the fit may be such that air is capable of passing between the outer surface 304 of the aerosol precursor consumable 300 and the inner surface of the inner frame 214 of the control unit 200. Thus, when a user puffs on the mouthpiece portion of the aerosol precursor consumable 300, air may pass between the outer surface 304 of the consumable 300 and the inner surface of the inner frame 214 and through an air entry 330 in the aerosol precursor consumable 300, mix with formed vapor near the atomizer 320, pass through the aerosol passage 316, and ultimately exit through an exit portal on the mouthpiece portion of the aerosol precursor consumable 300. The passage of air as defined above may be effective to cause pressure drop in the control unit 100 that can be sensed by the sensor through the aperture 215 in the receiving chamber 212.

In some implementations, the control unit may include one or more display elements, such as, for example, a digital display configured to convey information to a user. In some implementations, the control unit may include one or more user input elements, such as, for example, one or more buttons configured to operate one or more functions of the device. In some implementations, an input element may be included that replaces or supplements an airflow or pressure sensor. The input may be included to allow a user to control functions of the device and/or for output of information to a user. Any component or combination of components may be utilized as an input for controlling the function of the control unit 100. For example, one or more pushbuttons may be used as described in U.S. Pub. No. 2015/0245658 to Worm et al., which is incorporated herein by reference. Likewise, a touchscreen may be used as described in U.S. Pub. No. 2016/0262454 to Sears et al., which is incorporated herein by reference. As a further example, components adapted for gesture recognition based on specified movements of the aerosol delivery device may be used as an input. See U.S. Pub. No. 2016/0158782 to Henry et al., which is incorporated herein by reference. In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included, choosing the total particulate matter (TPM) provided per puff, choosing a specific heating profile to be implemented, choosing a modifiable resistance to drawn, and the like.

Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference. It is understood that not all of the illustrated elements are required. For example, an LED may be absent or may be replaced with a different indicator, such as a vibrating indicator.

As noted above, in other implementations, the aroma diffuser may have a different location and/or configuration. For example, FIG. 2 illustrates an aerosol delivery device 100 according to another example implementation of the present disclosure. In general, the aerosol delivery device 100 of the depicted implementation includes a control unit 200, and a removable aerosol precursor consumable 400. The removable aerosol precursor consumable 400 of the depicted implementation represents another example of an aerosol precursor consumable in the form of a liquid composition cartridge; however, aerosol precursor consumables of other implementations may differ. In the depicted implementation, the aerosol precursor consumable 400 is engageable with the control unit 200 to form an operating aerosol delivery device 100, and the aerosol precursor consumable 400 is removable therefrom.

In the depicted implementation, the control unit 200 is similar to the control unit 200 described with respect to FIG. 1. Reference is made, therefore, to that discussion, which will not be duplicated here. In the depicted implementation, the aerosol precursor consumable 400 comprises a cartridge that includes a liquid composition configured to produce an aerosol via electrically generated heat. In other implementations, other types of aerosol precursor consumables are possible. The aerosol precursor consumable 400 of the depicted implementation defines a body that includes an outer wall 404 and defines a distal end 406 and a proximal end 408. In the depicted implementation, mating connectors 410a, 410b are located proximate the distal end 406 of the aerosol precursor consumable 400 and are configured to form a connection with the mechanical connectors 224a, 224b present in the receiving chamber 212 of the control unit 200. As noted above, mechanical connectors of the control unit of some implementations may comprise magnetic elements. As such, the aerosol precursor consumable of some implementations may include mating magnetic connectors. Alternatively, or additionally, other complementary mechanical connectors may be located on the aerosol precursor consumable (e.g., on one or more sides of the outer wall and thus may be configured for establishing a friction fit or other mechanical fit with the receiving chamber of the control unit).

In the depicted implementation, the aerosol precursor consumable 400 is configured to contain an aerosol precursor composition for vaporization—i.e., an e-liquid, which may be configured as otherwise described herein. Reference is made to the discussion above with respect to the various possible aerosol precursor compositions and variations thereof. In the depicted implementation, the aerosol precursor consumable 400 includes an aerosol precursor composition reservoir 414 wherein the aerosol precursor composition may be retained. In the depicted implementation, an aerosol passage 416 at least partially surrounds the reservoir 414 in a longitudinal direction from the distal end 406 to the proximal end 408 of the consumable 400. In other implementations, however, it is understood that the aerosol passage may extend through at least a portion of the reservoir such that the reservoir is configured in an annular space between the aerosol passage and the consumable outer wall.

In the depicted implementation, the consumable 400 further includes a mouthpiece portion that is defined as a portion of the proximal end 408 of the consumable 400 that a user engages in order to draw on the device 100. Although in the depicted implementation the mouthpiece portion is integral with the consumable body 402, in other implementations the mouthpiece portion may be a separate element from the consumable body. In such implementations, the mouthpiece portion may be attachable to the consumable body. In the depicted implementation, the aerosol precursor consumable 400 further includes an atomizer 420 configured to aerosolize the aerosol precursor composition and that includes a liquid transport element 422. In the depicted implementation, the atomizer 420 comprises a heater and the liquid transport element 422 defines a fluid connection between the heater and liquid in the reservoir 414. In other implementations, the atomizer may comprise a vibrating assembly and the liquid transport element may define a fluid connection between the vibrating assembly and liquid in the reservoir.

In the depicted implementation, the atomizer 420 and liquid transport element 422 are configured as separate elements that are fluidly connected. In other implementations, these components may be combined. Still other implementations need not include a liquid transport element. In the depicted implementation, the aerosol precursor consumable 400 includes one or more electrical contacts 424a, 424b that are configured to electrically connect the atomizer 420 with the battery 216 in the control unit 200 through contact with the electrical pins 222a, 222b when the aerosol precursor consumable 400 is received in the receiving chamber 212 of the control unit 200.

In use, when an aerosol precursor consumable 400 is inserted into the receiving chamber 212 of the control unit 200, the fit may be such that air is capable of passing between the outer surface 404 of the aerosol precursor consumable 300 and the inner surface of the inner frame 214 of the control unit 200. Thus, when a user puffs on the mouthpiece portion of the aerosol precursor consumable 400, air may pass between the outer surface 404 of the consumable 400 and the inner surface of the inner frame 214 and through an air entry 430 in the aerosol precursor consumable 400, mix with formed vapor near the atomizer 420, pass through the aerosol passage 416, and ultimately exit through an exit portal on the mouthpiece portion of the aerosol precursor consumable 400. The passage of air as defined above may be effective to cause pressure drop in the control unit 100 that can be sensed by the sensor through the aperture 215 in the receiving chamber 212.

The aerosol precursor consumable 400 of the depicted implementation further includes an aroma diffuser 415 configured to diffuse an aroma composition for olfactory delivery to a user. In such a manner, the location of the aroma diffuser of some implementations may be positioned upstream from an aerosol outlet of the consumable. For example, in some implementations the aroma diffuser may be located proximate a user's nose when a user engages the consumable for delivery of the aerosol. In various implementations, the aroma diffuser may have any size or shape. In the depicted implementation, the aroma diffuser 415 has a substantially rectangular shape and rectangular cross-section and is located proximate the proximal end 408 of the aerosol precursor consumable 400, extending around the periphery of the consumable outer wall 404 (e.g., a strip that extends around the periphery of the consumable). In some implementations, the aroma composition may be impregnated into the aroma diffuser. In the depicted implementation, the aroma diffuser 415 is configured to transport (e.g., wick) the aroma composition from an aroma reservoir 417 for olfactory delivery to a user. In various implementations, the aroma diffuser may have a high porosity or a low porosity and may be made of a variety of materials or combinations of materials, including, but not limited to, polyethylene, polyethylene terephthalate, polypropylene, poly ether sulfone, cellulose, cotton, ceramics, silica, etc. In some implementations, the aroma diffuser may be made of fibers of these materials or fibers of combinations of materials. As noted, the aroma reservoir 417 of the depicted implementation is configured to store the aroma composition. In the depicted implementation, the aroma reservoir 417 is separate from the aerosol precursor composition reservoir 414, and is located at a position downstream (e.g., closer to the proximal end 408 of the aerosol precursor consumable 400) than the aerosol precursor composition reservoir 414. Reference is made to the discussion above with respect to the various possible aroma diffusers and materials thereof, as well as the various possible aroma compositions and variations thereof. In some implementations, the aroma diffuser may further include at least one temporary protective outer film configured to cover the aroma diffuser (such as, for example, during shipping and/or storage) and that is configured to be removed by a user.

As noted above, in other implementations, the aroma diffuser may have a different location and/or configuration. For example, FIG. 3 illustrates an aerosol delivery device according to another example implementation of the present invention. In general, the aerosol delivery device 100 of the depicted implementation includes a control unit 200, and a removable aerosol precursor consumable 500. The removable aerosol precursor consumable 500 of the depicted implementation represents another example of an aerosol precursor consumable in the form of a liquid composition cartridge; however, aerosol precursor consumables of other implementations may differ. In the depicted implementation, the aerosol precursor consumable 500 is engageable with the control unit 200 to form an operating aerosol delivery device 100, and the aerosol precursor consumable 500 is removable therefrom.

In the depicted implementation, the aerosol precursor consumable 500 comprises a cartridge that includes a liquid composition configured to produce an aerosol via electrically generated heat. In other implementations, other types of aerosol precursor consumables are possible. The aerosol precursor consumable 500 of the depicted implementation defines a body that includes an outer wall 504 and defines a distal end 506 and a proximal end 508. In the depicted implementation, mating connectors 510*a*, 510*b* are located proximate the distal end 506 of the aerosol precursor consumable 500 and are configured to form a connection with the mechanical connectors 224*a*, 224*b* present in the receiving chamber 212 of the control unit 200. As noted above, mechanical connectors of the control unit of some implementations may comprise magnetic elements. As such, the aerosol precursor consumable of some implementations may include mating magnetic connectors. Alternatively, or additionally, other complementary mechanical connectors may be located on the aerosol precursor consumable (e.g., on one or more sides of the outer wall and thus may be configured for establishing a friction fit or other mechanical fit with the receiving chamber of the control unit).

In the depicted implementation, the aerosol precursor consumable 500 is configured to contain an aerosol precursor composition for vaporization—i.e., an e-liquid, which may be configured as otherwise described herein. Reference is made to the discussion above with respect to the various possible aerosol precursor compositions and variations thereof. In the depicted implementation, the aerosol precursor consumable 500 includes an aerosol precursor composition reservoir 514 wherein the aerosol precursor composition may be retained. In the depicted implementation, an aerosol passage 516 at least partially surrounds the reservoir 514 in a longitudinal direction from the distal end 506 to the proximal end 508 of the consumable 500. In other implementations, however, it is understood that the aerosol passage may extend through at least a portion of the reservoir such that the reservoir is configured in an annular space between the aerosol passage and the consumable outer wall.

In the depicted implementation, the consumable 500 further includes a mouthpiece portion that is defined as a portion of the proximal end 508 of the consumable 500 that a user engages in order to draw on the device 100. Although in the depicted implementation the mouthpiece portion is integral with the consumable body 502, in other implementations the mouthpiece portion may be a separate element from the consumable body. In such implementations, the mouthpiece portion may be attachable to the consumable body. In the depicted implementation, the aerosol precursor consumable 500 further includes an atomizer 520 configured to aerosolize the aerosol precursor composition and that includes a liquid transport element 522. In the depicted implementation, the atomizer 520 comprises a heater and the liquid transport element 522 defines a fluid connection between the heater and liquid in the reservoir 514. In other implementations, the atomizer may comprise a vibrating assembly and the liquid transport element may define a fluid connection between the vibrating assembly and liquid in the reservoir.

In the depicted implementation, the atomizer 520 and liquid transport element 522 are configured as separate elements that are fluidly connected. In other implementations, these components may be combined. Still other implementations need not include a liquid transport element. In the depicted implementation, the aerosol precursor consumable 500 includes one or more electrical contacts 524*a*, 524*b* that are configured to electrically connect the atomizer 520 with the battery 216 in the control unit 200 through contact with the electrical pins 222*a*, 222*b* when the aerosol precursor consumable 400 is received in the receiving chamber 212 of the control unit 200.

In use, when an aerosol precursor consumable 500 is inserted into the receiving chamber 212 of the control unit

200, the fit may be such that air is capable of passing between the outer surface 504 of the aerosol precursor consumable 500 and the inner surface of the inner frame 214 of the control unit 200. Thus, when a user puffs on the mouthpiece portion of the aerosol precursor consumable 500, air may pass between the outer surface 504 of the consumable 500 and the inner surface of the inner frame 214 and through an air entry 530 in the aerosol precursor consumable 500, mix with formed vapor near the atomizer 520, pass through the aerosol passage 516, and ultimately exit through an exit portal on the mouthpiece portion of the aerosol precursor consumable 500. The passage of air as defined above may be effective to cause pressure drop in the control unit 200 that can be sensed by the sensor through the aperture 215 in the receiving chamber 212.

The aerosol precursor consumable 500 of the depicted implementation further includes an aroma diffuser 515 configured to diffuse an aroma composition for olfactory delivery to a user. In such a manner, the location of the aroma diffuser of some implementations may be positioned upstream from an aerosol outlet of the consumable. For example, in some implementations the aroma diffuser may be located proximate a user's nose when a user engages the consumable for delivery of the aerosol. In various implementations, the aroma diffuser may have any size or shape. In the depicted implementation, the aroma diffuser 515 has a substantially rectangular shape and rectangular cross-section, extending around the periphery of the consumable outer wall 504 (e.g., a strip that extends around the periphery of the consumable). In some implementations, the aroma composition may be impregnated into the aroma diffuser. In the depicted implementation, the aroma diffuser 515 is configured to transport (e.g., wick) the aroma composition from an aroma reservoir 517 for olfactory delivery to a user. In various implementations, the aroma diffuser may have a high porosity or a low porosity and may be made of a variety of materials or combinations of materials, including, but not limited to, polyethylene, polyethylene terephthalate, polypropylene, poly ether sulfone, cellulose, cotton, ceramics, silica, etc. In some implementations, the aroma diffuser may be made of fibers of these materials or fibers of combinations of materials. As noted, the aroma reservoir 517 of the depicted implementation is configured to store the aroma composition. In the depicted implementation, the aroma reservoir 517 is separate from the aerosol precursor composition reservoir 514, and surrounds at least a portion of the aerosol precursor composition reservoir 514 to form an annular storage area. Reference is made to the discussion above with respect to the various possible aroma diffusers and materials thereof, as well as the various possible aroma compositions and variations thereof. In some implementations, the aroma diffuser may further include at least one temporary protective outer film configured to cover the aroma diffuser (such as, for example, during shipping and/or storage) and that is configured to be removed by a user.

In the depicted implementation, the control unit 200 is similar to the control unit 200 described with respect to FIG. 1. Reference is made, therefore, to that discussion, which will not be duplicated here. In addition, the control unit 200 of the depicted implementation also includes a plurality of apertures 230 that extend through the control unit outer wall 204 and into the receiving chamber 212. Although other implementation may include a single opening, the depicted implementation includes a plurality of apertures 230 located on opposite sides of the control unit 200. In such a manner, when the aerosol precursor consumable 500 is engaged with the control unit 200, the aroma diffuser 515 is configured to be located proximate (e.g., underneath) the plurality of apertures 230 of the control unit body frame 202 such that olfactory delivery of the aroma may occur through the apertures 230. It should be noted that some implementations need not include any openings extending through the control unit outer wall. In such a manner, olfactory delivery of the aroma may occur through a gap that extends around at least a portion of the consumable at the interface between the consumable and the control unit proximate the opening of the receiving chamber.

As noted above, in other implementations, the aroma diffuser may have a different location and/or configuration. For example, FIG. 4 illustrates an aerosol delivery device according to another example implementation of the present invention. In general, the aerosol delivery device 100 of the depicted implementation includes a control unit 200, and a removable aerosol precursor consumable 600. The removable aerosol precursor consumable 600 of the depicted implementation represents another example of an aerosol precursor consumable in the form of a liquid composition cartridge; however, aerosol precursor consumables of other implementations may differ. In the depicted implementation, the aerosol precursor consumable 600 is engageable with the control unit 200 to form an operating aerosol delivery device 100, and the aerosol precursor consumable 600 is removable therefrom.

In the depicted implementation, the control unit 200 is similar to the control unit 200 described with respect to FIG. 1. Reference is made, therefore, to that discussion, which will not be duplicated here. In the depicted implementation, the aerosol precursor consumable 600 comprises a cartridge that includes a liquid composition configured to produce an aerosol via electrically generated heat. In other implementations, other types of aerosol precursor consumables are possible. The aerosol precursor consumable 600 of the depicted implementation defines a body that includes an outer wall 604 and defines a distal end 606 and a proximal end 608. In the depicted implementation, mating connectors 610a, 610b are located proximate the distal end 606 of the aerosol precursor consumable 600 and are configured to form a connection with the mechanical connectors 224a, 224b present in the receiving chamber 212 of the control unit 200. As noted above, mechanical connectors of the control unit of some implementations may comprise magnetic elements. As such, the aerosol precursor consumable of some implementations may include mating magnetic connectors. Alternatively, or additionally, other complementary mechanical connectors may be located on the aerosol precursor consumable (e.g., on one or more sides of the outer wall and thus may be configured for establishing a friction fit or other mechanical fit with the receiving chamber of the control unit).

In the depicted implementation, the aerosol precursor consumable 600 is configured to contain an aerosol precursor composition for vaporization—i.e., an e-liquid, which may be configured as otherwise described herein. Reference is made to the discussion above with respect to the various possible aerosol precursor compositions and variations thereof. In the depicted implementation, the aerosol precursor consumable 600 includes an aerosol precursor composition reservoir 614 wherein the aerosol precursor composition may be retained. In the depicted implementation, an aerosol passage 616 at least partially surrounds the reservoir 614 in a longitudinal direction from the distal end 606 to the proximal end 608 of the consumable 600. In other implementations, however, it is understood that the aerosol passage may extend through at least a portion of the reservoir such that the reservoir is configured in an annular space between the aerosol passage and the consumable outer wall.

In the depicted implementation, the consumable 600 further includes a mouthpiece portion that is defined as a portion of the proximal end 408 of the consumable 600 that a user engages in order to draw on the device 100. Although in the depicted implementation the mouthpiece portion is integral with the consumable body 602, in other implementations the mouthpiece portion may be a separate element from the consumable body. In such implementations, the mouthpiece portion may be attachable to the consumable body. In the depicted implementation, the aerosol precursor consumable 600 further includes an atomizer configured to aerosolize the aerosol precursor composition and that includes a liquid transport element 622. In the depicted implementation, the atomizer 620 comprises a heater and the liquid transport element 622 defines a fluid connection between the heater and liquid in the reservoir 614. In other implementations, the atomizer may comprise a vibrating assembly and the liquid transport element may define a fluid connection between the vibrating assembly and liquid in the reservoir.

In the depicted implementation, the atomizer 620 and liquid transport element 622 are configured as separate elements that are fluidly connected. In other implementations, these components may be combined. Still other implementations need not include a liquid transport element. In the depicted implementation, the aerosol precursor consumable 600 includes one or more electrical contacts 624a, 624b that are configured to electrically connect the atomizer 620 with the battery 216 in the control unit 200 through contact with the electrical pins 222a, 222b when the aerosol precursor consumable 600 is received in the receiving chamber 212 of the control unit 200.

In use, when an aerosol precursor consumable 600 is inserted into the receiving chamber 212 of the control unit 200, the fit may be such that air is capable of passing between the outer surface 604 of the aerosol precursor consumable 600 and the inner surface of the inner frame 214 of the control unit 200. Thus, when a user puffs on the mouthpiece portion of the aerosol precursor consumable 600, air may pass between the outer surface 604 of the consumable 600 and the inner surface of the inner frame 214 and through an air entry 630 in the aerosol precursor consumable 600, mix with formed vapor near the atomizer 620, pass through the aerosol passage 616, and ultimately exit through an exit portal on the mouthpiece portion of the aerosol precursor consumable 600. The passage of air as defined above may be effective to cause pressure drop in the control unit 200 that can be sensed by the sensor through the aperture 215 in the receiving chamber 212.

The aerosol precursor consumable 600 of the depicted implementation further includes a plurality of aroma diffusers 615 configured to diffuse an aroma composition for olfactory delivery to a user. In particular, the aerosol precursor consumable 600 of the depicted implementation includes four aroma diffusers, one on each side of the consumable outer surface 604. In such a manner, the location of the aroma diffuser(s) of some implementations may be positioned upstream from an aerosol outlet of the consumable. For example, in some implementations the aroma diffuser(s) may be located proximate a user's nose when a user engages the consumable for delivery of the aerosol. In various implementations, the aroma diffuser may have any size or shape. In the depicted implementation, the aroma diffusers 615 have substantially rectangular or square shapes (with rectangular cross-sections). In some implementations, the aroma composition may be impregnated into the aroma diffuser(s). In some implementations having multiple aroma diffusers, each aroma diffuser may be associated with a different aroma composition. In such a manner, two or more aroma compositions may be mixed and/or matched with each other in any combination, or the aroma compositions may be used individually on demand by a user. For example, a user may rotate the cartridge in order to place a desired aroma closer to the user's nose. In some implementations, visual indicators may be used to identify and/or differentiate the different aroma compositions.

In the depicted implementation, the plurality of aroma diffusers 615 are configured to transport (e.g., wick) aroma compositions from a plurality of aroma reservoirs 617 for olfactory delivery to a user. It should be noted that although in the depicted implementation each aroma diffuser is associated with a respective aroma reservoir, in other implementations two or more (or all) of the aroma diffusers may be associated with a common aroma reservoir. In any event, in some implementations two or more of the aroma reservoirs may include the same aroma composition, while in other implementations, two or more of the aroma reservoirs may include different aroma compositions.

In various implementations, the aroma diffusers may have a high porosity or a low porosity and may be made of a variety of materials or combinations of materials, including, but not limited to, polyethylene, polyethylene terephthalate, polypropylene, poly ether sulfone, cellulose, cotton, ceramics, silica, etc. In some implementations, the aroma diffuser may be made of fibers of these materials or fibers of combinations of materials. In some implementations, two or more of the aroma diffusers may be made of the same material. In other implementations, two or more of the aroma diffusers may be made of different materials. In the depicted implementation, the aroma reservoirs 617 are separate from the aerosol precursor composition reservoir 614, and the plurality of aroma reservoirs 617 surround at least a portion of the aerosol precursor composition reservoir 614. Reference is made to the discussion above with respect to the various possible aroma diffusers and materials thereof, as well as the various possible aroma compositions and variations thereof. In some implementations, the aroma diffuser may further include at least one temporary protective outer film, or a plurality of respective temporary protective outer films, configured to cover the aroma diffuser (such as, for example, during shipping and/or storage) and that is configured to be removed by a user.

As noted above, the aerosol precursor consumable of the present disclosure may have may different forms and shapes. Another example of an aerosol precursor consumable is shown in FIG. 5. In particular, FIG. 5 illustrates an aerosol precursor consumable 700 according to another example implementation of the present disclosure. The removable aerosol precursor consumable 700 of the depicted implementation represents another example of an aerosol precursor consumable in the form of a liquid composition cartridge; however, aerosol precursor consumables of other implementations may differ. In the depicted implementation, the aerosol precursor consumable 700 is engageable with a control unit to form an operating aerosol delivery device, and the aerosol precursor consumable 700 is removable therefrom. In various implementations, the control unit may be similar to the control units described above.

In the depicted implementation, the aerosol precursor consumable 700 comprises a cartridge that includes a liquid composition configured to produce an aerosol via electrically generated heat. The aerosol precursor consumable 700 of the depicted implementation defines a body that includes an outer wall 704 and defines a distal end 706 and a proximal end 708. In the depicted implementation, mating connectors 710a, 710b are located proximate the distal end 706 of the aerosol precursor consumable 700 and are configured to form a connection with the mechanical connectors present in the receiving chamber of a control unit. As noted above, mechanical connectors of the control unit of some implementations may comprise magnetic elements. As such, the aerosol precursor consumable of some implementations may include mating magnetic connectors. Alternatively, or additionally, other complementary mechanical connectors may be located on the aerosol precursor consumable (e.g., on one or more sides of the outer wall and thus may be configured for establishing a friction fit or other mechanical fit with the receiving chamber of the control unit).

In the depicted implementation, the aerosol precursor consumable 700 is configured to contain an aerosol precursor composition for vaporization—i.e., an e-liquid, which may be configured as otherwise described herein. Reference is made to the discussion above with respect to the various possible aerosol precursor compositions and variations thereof. In the depicted implementation, the aerosol precursor consumable 700 includes an aerosol precursor composition reservoir 714 wherein the aerosol precursor composition may be retained. In the depicted implementation, the aerosol precursor composition reservoir 714 surrounds a substantially centrally located aerosol passage 716 that extends in a longitudinal direction from the atomizer 720 to an opening at the proximal end 708 of the consumable 700 such that the reservoir 714 is configured in an annular space between the aerosol passage 716 and the consumable outer wall 704. In other implementations, however, it is understood that the aerosol passage may extend around the reservoir.

In the depicted implementation, the consumable 700 further includes a mouthpiece portion 725 that is defined as a portion of the proximal end 708 of the consumable 700 that a user engages in order to draw on the device 100. Although in the depicted implementation, the mouthpiece portion is separate from the consumable body and is attachable and removable therefrom, in other implementations, the mouthpiece portion may be integral with the consumable body. In the depicted implementation, the aerosol precursor consumable 700 further includes an atomizer 720 configured to aerosolize the aerosol precursor composition and that includes a liquid transport element. In the depicted implementation, the atomizer 720 comprises a heater and the liquid transport element defines a fluid connection between the heater and liquid in the reservoir 714. In other implementations, the atomizer may comprise a vibrating assembly and the liquid transport element may define a fluid connection between the vibrating assembly and liquid in the reservoir.

In the depicted implementation, the atomizer 720 and liquid transport element are configured as separate elements that are fluidly connected. In other implementations, these components may be combined. Still other implementations need not include a liquid transport element. In the depicted implementation, the connectors 710a, 710b of the consumable 700 also serve as electrical contacts that are configured to electrically connect the atomizer 720 with the battery of the control unit through contact with electrical contacts thereof, when the aerosol precursor consumable 700 is received in the receiving chamber of the control unit.

In use, when an aerosol precursor consumable 700 is inserted into the receiving chamber of a control unit, the fit may be such that air is capable of passing between the outer surface 704 of the aerosol precursor consumable 700 and an inner surface of the control unit. Thus, when a user puffs on the mouthpiece portion 725 of the aerosol precursor consumable 700, air may pass between the outer surface 704 of the consumable 700 and the inner surface of the control unit and through an air entry 730 in the aerosol precursor consumable 700, mix with formed vapor near the atomizer 720, pass through the aerosol passage 716, and ultimately exit through an exit portal on the mouthpiece portion of the aerosol precursor consumable 700. The passage of air as defined above may be effective to cause pressure drop in the control unit that can be sensed by a sensor.

The aerosol precursor consumable 700 of the depicted implementation further includes an aroma diffuser 715 configured to diffuse an aroma composition for olfactory delivery to a user. In the depicted implementation, the aerosol precursor consumable 700 includes a single aroma diffuser 715 located in a recess 727 defined in the outer wall 704 of the consumable 700. In particular, the aroma diffuser 715 is located upstream from the mouthpiece portion 725 such that the aroma diffuser 715 is located proximate a user's nose when a user engages the mouthpiece portion 725 for delivery of the aerosol. In various implementations, the aroma diffuser may have any size or shape. In the depicted implementation, the aroma diffuser 715 has a curved shape and extends around the periphery of the consumable outer wall 704. In the depicted implementation, the aroma composition is impregnated into the aroma diffuser 715 for olfactory delivery to a user, and there is not a separate aroma reservoir. In other implementations, one or more aroma diffusers may be configured to transport (e.g., wick) aroma compositions from a one or more aroma reservoirs.

In various implementations, the aroma diffusers may have a high porosity or a low porosity and may be made of a variety of materials or combinations of materials, including, but not limited to, polyethylene, polyethylene terephthalate, polypropylene, poly ether sulfone, cellulose, cotton, ceramics, silica, etc. In some implementations, the aroma diffuser may be made of fibers of these materials or combinations of materials. In some implementations, two or more of the aroma diffusers may be made of the same material. In other implementations, two or more of the aroma diffusers may be made of different materials. In some implementations, the consumable may initially include at least one temporary protective outer film configured to cover one or more of the aroma diffusers and that may be removed by a user. Reference is made to the discussion above with respect to the various possible aroma diffusers and materials thereof, as well as the various possible aroma compositions and variations thereof.

In one or more implementations, the present disclosure may be directed to kits that provide a variety of components as described herein. For example, a kit may comprise a control unit with one or more aerosol precursor consumables. A kit may further comprise a control unit with one or more aerosol precursor consumables and one or more aroma diffusers. A kit may further comprise a control unit with one or more charging components. A kit may further comprise a control unit with one or more power sources. A kit may further comprise a control unit with one or more aerosol precursor consumables and one or more charging components and/or one or more power sources. A kit may further comprise a plurality of aerosol precursor consumables. In further implementations, a kit may comprise a plurality of aroma diffusers. A kit may further comprise a plurality of aroma diffusers and one or more aerosol precursor consumables. A kit may further comprise a plurality of aerosol precursor consumables and one or more power sources and/or one or more charging components. In the above implementations, the aerosol precursor consumables or the control units may be provided with an atomizer inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:
    a control unit that defines a housing having a proximal end and a distal end, the proximal end of the housing defining a receiving chamber;
    at least one aroma aperture extending through the housing into the receiving chamber proximate the proximal end; and
    a removable and replaceable aerosol precursor consumable, at least a portion of the consumable configured to be received into the receiving chamber, the aerosol precursor consumable comprising:
      a housing defining an outer wall;
      an aerosol precursor composition reservoir located in the housing and configured to contain an aerosol precursor composition;
      an atomizer located in the housing; and
      at least one aroma diffuser,
    wherein the atomizer is configured to vaporize the aerosol precursor composition to generate an aerosol for oral delivery to a user, wherein the at least one aroma diffuser is configured to diffuse an aroma composition for olfactory delivery to the user, and wherein when the aerosol precursor consumable is engaged with the control unit, the aroma diffuser is positioned proximate the at least one aroma aperture in the control unit housing, such that the aroma composition is delivered to the user through the at least one aroma aperture.

2. The aerosol delivery device of claim 1, wherein the at least one aroma aperture comprises a plurality of aroma apertures.

3. The aerosol delivery device of claim 1, wherein the at least one aroma diffuser is located in a recess defined in the outer wall of the aerosol precursor consumable housing.

4. The aerosol delivery device of claim 1, further comprising a mouthpiece portion, and wherein the aroma diffuser is located upstream from the mouthpiece portion.

5. The aerosol delivery device of claim 1, wherein when a user engages the mouthpiece portion of the aerosol precursor consumable, the aroma diffuser is positioned proximate the user's nose.

6. The aerosol delivery device of claim 1, further comprising at least one aroma reservoir located in the aerosol precursor consumable housing and configured to contain the aroma composition.

7. The aerosol delivery device of claim 6, wherein the at least one aroma reservoir comprises a plurality of aroma reservoirs, wherein the at least one aroma diffuser comprises a plurality of aroma diffusers, and wherein respective ones of the plurality of aroma diffusers are in liquid communication with respective ones of the plurality of aroma reservoirs.

8. The aerosol delivery device of claim 1, wherein the at least one aroma reservoir surrounds at least a portion of the aerosol precursor composition reservoir.

9. The aerosol delivery device of claim 1, wherein the aerosol precursor composition comprises an unflavored aerosol precursor composition.

10. The aerosol delivery device of claim 1, wherein the at least one aroma diffuser includes at least one temporary protective outer film configured to be removed by a user.

* * * * *